United States Patent
Laghi (12)

(10) Patent No.: US 6,454,812 B1
(45) Date of Patent: Sep. 24, 2002

(54) APPARATUS AND METHOD FOR ATTACHING A DISTAL UMBRELLA TO A GEL PROSTHETIC LINER

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 83 days.

(21) Appl. No.: 09/630,509

(22) Filed: Aug. 2, 2000

Related U.S. Application Data

(63) Continuation-in-part of application No. 09/318,416, filed on May 25, 1999, now abandoned.

(51) Int. Cl.[7] .................................................. A61F 2/80
(52) U.S. Cl. ........................................................ 623/36
(58) Field of Search ..................................... 623/32–38

(56) References Cited

U.S. PATENT DOCUMENTS

| | | | | |
|---|---|---|---|---|
| 5,830,237 | A | * 11/1998 | Kania | 623/37 |
| 5,957,980 | A | * 9/1999 | Houser et al. | 623/36 |
| 6,156,071 | A | * 12/2000 | Biedermann et al. | 623/33 |
| 6,231,617 | B1 | * 5/2001 | Fay | 623/36 |
| 6,406,499 | B1 | * 6/2002 | Kania | 623/36 |

FOREIGN PATENT DOCUMENTS

| | | | |
|---|---|---|---|
| WO | WO 99/60958 | * 12/1999 | 623/36 |

* cited by examiner

Primary Examiner—David H. Willse
(74) Attorney, Agent, or Firm—Ronald E. Smith; Smith & Hopen, P.A.

(57) ABSTRACT

A prosthetic liner made of gel has an externally mounted fabric reinforcement at its distal end to limit pistoning of the residual limb. The fabric is substantially inextensible in a longitudinal direction but is extensible in a radial direction relative to the longitudinal axis of the residual limb. The fabric is provided in a single layer in one embodiment and in a double layer in a second embodiment, but in all embodiments a distal umbrella is secured to a distal end of the liner. A distal umbrella has a base embedded in the gel in a first embodiment. The base is disposed in overlying relation to the gel and in underlying relation to the fabric in a second embodiment. The gel is thickened at the distal end of the liner so that the durability and comfort level of the liner compares favorably with the durability and comfort of silicone liners. The liner is as easy to put on and take off as a sock, there being no need to roll the its liner onto the residual limb. A novel method for making the liner facilitates thickening the distal end of the liner because the method does not require the liner to be turned inside out during the manufacturing process or upon completion of the manufacturing process.

21 Claims, 4 Drawing Sheets

APPARATUS AND METHOD FOR ATTACHING A DISTAL UMBRELLA TO A GEL PROSTHETIC LINER

CROSS-REFERENCE TO RELATED DISCLOSURES

This disclosure is a continuation-in-part of a disclosure entitled Gel Prosthetic Liner with Distal Umbrella, application Ser. No. 09/318,416, filed May 05, 1999 by the present inventor, now abandoned.

BACKGROUND OF THE INVENTION

1. Field of the Invention

This invention relates, generally, to the art of prosthetics. More particularly, it relates to an improvement in prosthetic liners of the type made from gel, reinforced by a stretchable fabric, and having a distal umbrella that enables interconnection between the liner and a prosthetic device.

2. Description of the Prior Art

Gels have been used in prosthetic interfaces since the late 1980's. However, gels are relatively weak and cannot be used for most purposes without a fabric reinforcement. Accordingly, they are almost always used in conjunction with a fabric. Even when reinforced with fabric, most gels still break down in intensive use such as long distance running.

The most suitable fabrics for reinforcing gel liners are stretchable to enable stretching of the gel liner; the inherent strength of the fabric reinforces the gel liner.

Various distal attachment means, referred to hereinafter as distal umbrellas due to their shape, have been developed to attach the distal end of a gel/fabric combination to a prosthetic device. Significantly, the prior art teaches that the distal umbrella is mounted to an external, outside surface of the fabric. In some constructions, the distal attachment means is simply glued or otherwise attached to said exterior surface. Alternatively, a threaded aluminum nut is insert molded onto an external surface of the fabric by injection molding a thermoplastic polymer over the nut and the fabric that covers the gel. This molding operation is performed after the gel has been applied to the inside surface of the fabric.

There are two primary drawbacks to liners of this type. The first drawback is that no gel pad cushion is provided at the distal end of the liner. The second shortcoming is that the strength of the attachment is only as strong as the bond between the distal umbrella and the fabric or the bond between the molded thermoplastic polymer and the fabric.

Both of these limitations are a result of the manufacturing process used to make the fabric-covered liner. In the molding operation, the fabric cover is inverted and placed over a metal mandrel. The mandrel is then introduced into a mold cavity. If injection molding is employed, the mold cavity is filled with molten thermoplastic prior to the intriction of the mandrel into the mold cavity. If compression molding or open mold injection molding is employed, the mold cavity is filled with molten thermoplastic after introduction of the mandrel into the mold cavity. A mandrel having fabric on it is then introduced into the mold. The mold is cooled until the gel solidifies; it is then opened and the gel liner is removed from the mandrel and inverted to its right side out configuration.

If the fabric-covered liner is made by a dipping process, sometimes referred to as dip molding, the mandrel covered with a fabric is dipped several times in a gel bath with the mandrel itself being cooled. The gel deposits itself onto the fabric and solidifies on said fabric. The thickness of the gel coating on the fabric is determined by the temperature of the molten gel bath, the viscosity of the gel, the number of dips, and the temperature of the mandrel.

In both techniques (molding and dipping), the last step of the manufacturing process requires turning the liner inside out so that the gel is on the inside of the liner, in contact with the residual limb. A thick pad at the distal end cannot be provided because it would prevent such inside-out turning of the liner. Nor has the art developed a way to embed the base of the distal umbrella within the gel. If the base could be embedded, such structural feature would provide an enhanced connection between the distal umbrella and the liner.

Accordingly, there is a need for a gel liner having a fabric cover and a thick pad at its distal end and for a new method of making a gel liner having a fabric cover and a thick pad of gel at its distal end. The new method should not require that the liner be turned inside-out at the end of the manufacturing process, or at any other stage thereof.

Moreover, there is a need for an improved method of securing a distal umbrella to the distal end of a liner. Specifically, there is a need for a means for attaching a distal umbrella to the inside of the fabric instead of the outside thereof. Moreover, there is a need for a method that would enable the base of a distal umbrella to be embedded within the gel.

However, in view of the art considered as a whole at the time the present invention was made, it was not obvious to those of ordinary skill in this art how these needs could be fulfilled.

SUMMARY OF THE INVENTION

The long-standing but heretofore unfulfilled need for an apparatus that overcomes the limitations of the prior art is now met by a new, useful, and nonobvious invention. The invention meets the need for a new manufacturing method capable of producing a gel liner having a fabric cover and a thick, cushioned distal end. It also provides methods for improving the connection between the liner and the distal umbrella.

The present invention is a prosthetic liner made of gel where the thickness of the gel is increased at the distal end thereof and wherein fabric reinforces the distal end to reduce pistoning of the residual limb. A distal umbrella having a base and a neck is secured to the distal end of the liner to enable connection of the liner to an artificial leg that includes an artificial foot. In a first embodiment, the base of the distal umbrella is embedded within the thickened part of the gel. In a second embodiment, the base of the distal umbrella overlies an exterior surface of the gel and underlies the fabric.

The gel is a foamed or non-foamed gel composition including a block copolymer and mineral oil.

The fabric is secured to the gel near the distal end of the prosthetic liner to limit pistoning of the distal end of a residual limb during ambulation, and the distal umbrella is secured to said distal end of the prosthetic liner to facilitate connection of the liner to another prosthetic device such as an artificial leg and foot. The fabric may be secured to an exterior surface of the liner and the fabric may extend the entire longitudinal extent of the liner or just a predetermined extent thereof. Preferably, the fabric is secured to an exterior surface of the liner in the region of the distal end of the liner, extending from the distal end a distance between about three to six inches toward the proximal end of the liner.

Alternatively, the fabric may be embedded within the liner along the entire longitudinal extent thereof, or along a predetermined extent thereof. Preferably, when the fabric is embedded, it is embedded in the region of the distal end of the liner, extending from the distal end a distance between about three to six inches toward a proximal end thereof.

The preferred fabric is a nylon-lycra combination having a first, limited extensibility in a longitudinal direction and having a second, greater extensibility in a direction radial to the longitudinal direction. The preferred combination includes 85% to 95% nylon and 5% to 15% lycra. The fabric may be provided in a single layer that is stitched or adhered to the exterior surface of the gel liner. Alternatively, the fabric may be provided in a double layer, including a first and a second layer, wherein the first and second layers of fabric are joined to one another and to the gel liner by stitching or by an elastic adhesive. Moreover, the fabric may be embedded within the gel.

The distal umbrella includes a disc or umbrella-shaped base and a neck or stem that depends from the center thereof. An internally threaded central bore is formed in the stem for engagement with an externally threaded pin that forms a part of a prosthesis.

There are numerous mechanical means for attaching the distal umbrella to the gel liner, and all such means are within the scope of this invention as long as the base of the distal umbrella is embedded within the gel or attached to the interior surface of the fabric in overlying relation to the exterior surface of the gel liner. In both cases, an elongate neck of the distal umbrella extends through a suitable opening formed in the distal end of the fabric to enable attachment of a prosthetic leg to said neck.

For example, a metallic grommet member may be used to secure the peripheral edge of the fabric that surrounds said opening to the neck of the distal umbrella. Alternatively, said peripheral edge of the fabric may be bonded to a plastic grommet member by melting or by high frequency welding. The metallic or plastic grommet members have utility in the embodiment where the base of the distal umbrella is embedded in the fabric and in the embodiment where said base overlies the exterior surface of the gel and underlies the fabric.

A metallic or textile ring that encircles the stem can also be used to anchor the peripheral edge of the fabric to the neck of the distal umbrella in both the embedded and surface-mounted embodiments.

An annular groove may also be formed in the base of the distal umbrella, and the peripheral edge of the fabric that surrounds said neck opening may be positioned within said annular groove and secured thereto by crimping shut said groove in locking relation to said fabric. This particular attachment means has primary utility in the surface-mounted embodiment.

The novel liner does not require forming over a plaster model and thus eliminates the need for several time-consuming and costly operations by the prosthetist. This feature also allows the patient to be fitted in the first office visit.

The novel liner is less costly to manufacture because the manufacturing process requires only a molding operation. Savings include the cost of the fabric, and also of the cutting, sewing and placing of the fabric in the mold. The rate of rejects is also reduced as fewer manufacturing operations are involved.

In approximately 70% of the cases where a patient needs fitting with a gel liner, and where the patient has already been provided with a hard socket, the novel liner can be donned by the patient and the residual limb introduced into the existing socket and the amputee will report a better fit than with the original liner, due to the superior conforming characteristics of the novel liner. This provides a significant economic advantage because no new hard socket is required. Moreover, the amputee is fitted within a few minutes during the first office visit.

Since the novel liner avoids the need for modification of an existing hard socket, in most cases, the prosthetist simply needs to take a negative cast of the residual limb with the novel liner on, make a positive plaster model from it, and from the positive model make the hard socket without making modifications to the positive plaster model.

The primary object of this invention is to advance the art of fabric-covered gel liners.

Another broad object is to advance the art of making fabric-covered gel liners having distal ends where the gel is thickened for cushioning purposes.

A more specific object is to advance the art of attaching distal umbrellas to the distal end of fabric-covered gel liners.

Another important object is to provide a fabric-covered gel liner having a distal umbrella where the base of the distal umbrella is embedded within the gel at the distal end of the gel liner.

Another object is to provide a fabric-covered gel liner having a distal umbrella where the base of the distal umbrella is attached to the interior side of the fabric that covers the gel liner.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWING

For a fuller understanding of the nature and objects of the invention, reference should be made to the following detailed description, taken in connection with the accompanying drawing, in which.

DETAILED DESCRIPTION OF THE PREFERRED EMBODIMENT

Figure 1:
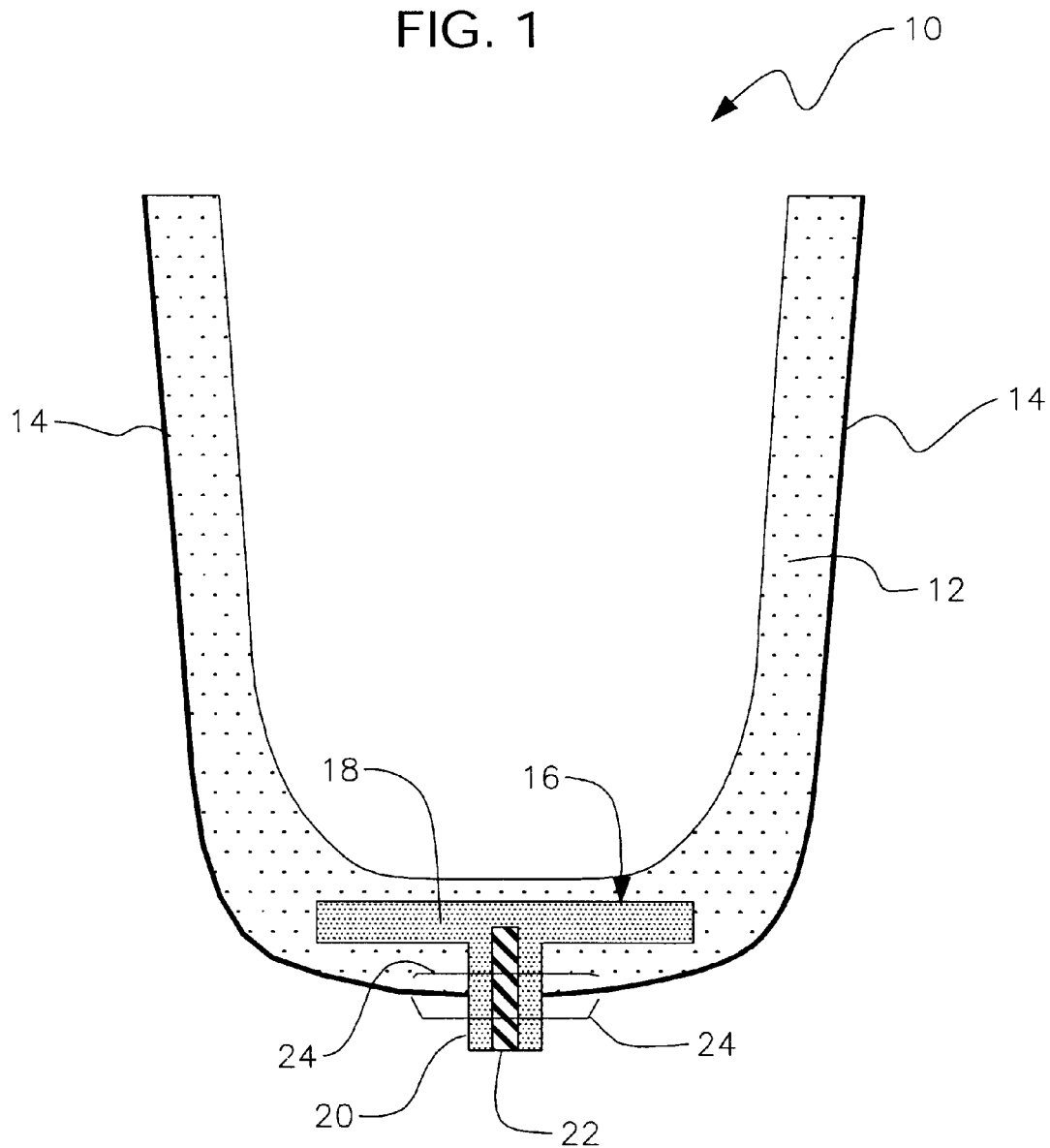
FIG. 1 is a sectional view of a novel gel liner having a fabric-reinforced distal end and a distal umbrella where the fabric is secured to the stem of the distal umbrella by a grommet.

Referring now to FIG. 1, it will there be seen that an exemplary embodiment of the invention is denoted as a whole by the reference numeral 10. The gel part of the liner is denoted 12, a fabric cover or reinforcement is denoted 14, and a distal umbrella is denoted 16 as a whole. Distal umbrella 16 may be formed of a metallic or other rigid material. Distal umbrella 16 further includes a generally disc-shaped base 18 and a hollow stem 20. Base 18 is drawn flat, but it should be understood that it is typically of umbrella-like configuration so that it conforms to the rounded distal end of liner 10. Internally-threaded central bore 22 is formed in stem 20 and receives an externally-threaded screw, not shown, that surmounts a prosthesis in a well-known way.

In this embodiment, base 16 and part of neck 20 are embedded within gel 12. Neck 20 extends through a suitable opening formed in fabric 14.

An annular groove is preferably formed in a part of stem 20 that is not embedded in gel 12; said groove is not numbered to avoid cluttering the drawing. The central aperture of brass grommet 24 receives stem 20 and the internal peripheral edge of the grommet that surrounds said central aperture is received within the annular groove formed in stem 20. The diameter of stem 20 slightly exceeds the diameter of the central aperture of grommet 24. Thus, the grommet is slideably forced onto stem 20 until said internal peripheral edge of the grommet pops into the unnumbered annular groove. The peripheral edge of fabric 14 that surrounds the neck-receiving opening thereof is then positioned between the open jaws of grommet 24 and suitable crimping means are employed to crimp said jaws shut in tightly engaging relation to said fabric.

It should be understood from FIG. 1 that grommet 24 engages fabric 14 in the same way if base 16 of distal umbrella 16 is not embedded within gel 12, i.e., if said base overlies an exterior surface of gel 12 and underlies fabric 14.

An alternative construction employs a plastic grommet (preferably nylon) joined to fabric 14 by melting or high frequency welding.

There are numerous other ways of performing the mechanical interconnection of fabric 14 to distal umbrella 16.

Figure 2:
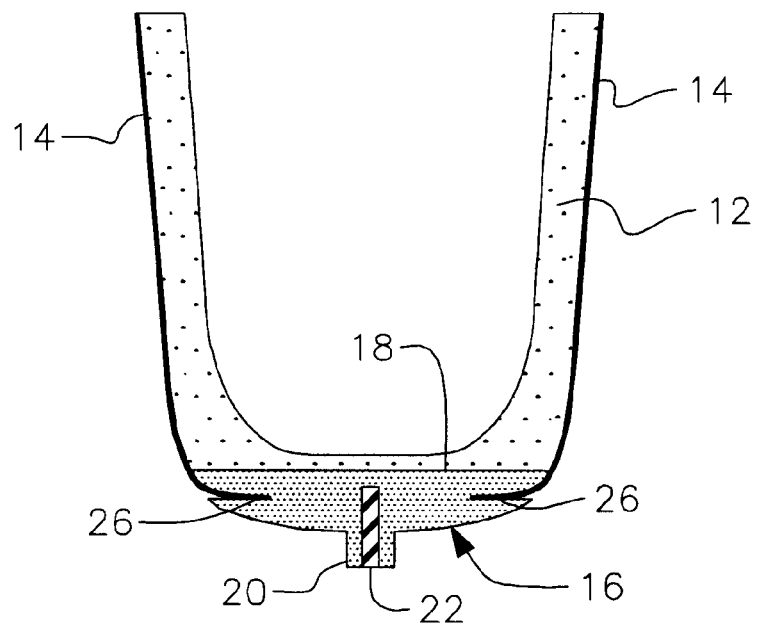
FIG. 2 is a sectional view of a novel gel liner having a fabric-reinforced distal end and a distal umbrella where the fabric is crimped into an annular groove formed in the base of the distal umbrella.

For example, in FIG. 2 grommet 24 is eliminated and a peripheral groove 26 is formed in base 18 of distal umbrella 16. The peripheral edge of fabric 14 that surrounds the central opening formed therein is positioned within said peripheral groove 26 and the groove is then crimped shut by a suitable crimping means to securely capture the fabric therein. This attachment means applies primarily to those embodiments where distal umbrella 16 is not embedded within gel 12.

Figure 3:
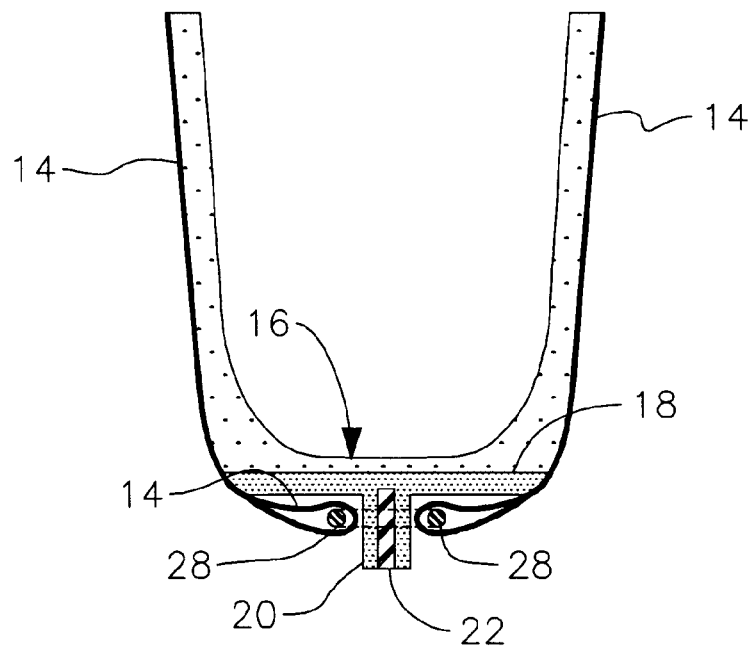
FIG. 3 is a sectional view of a novel gel liner having a fabric-reinforced distal end and a distal umbrella where the fabric is secured to the stem of the distal umbrella by a ring.
Figure 4:
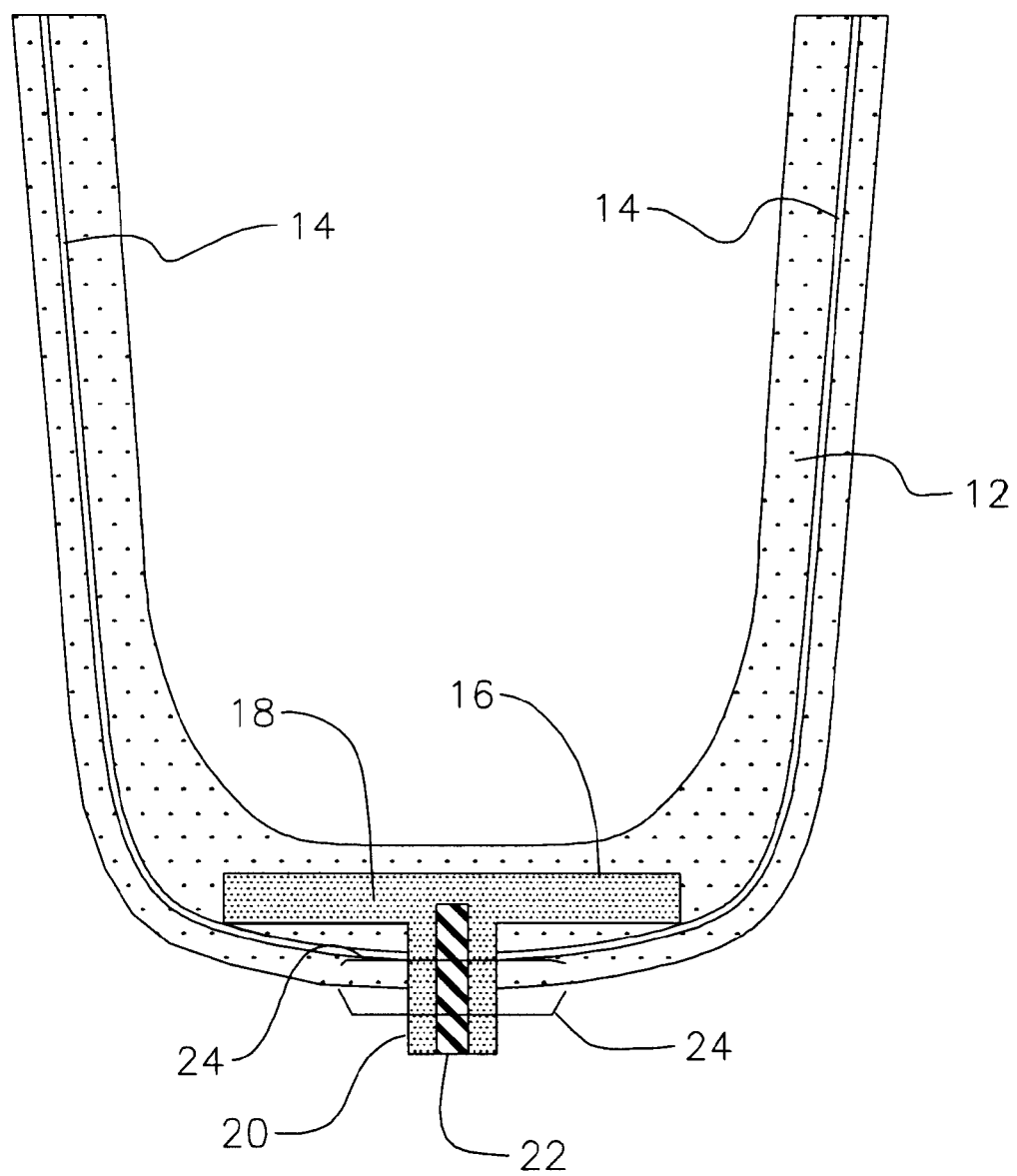
FIG. 4 is a sectional view of an embodiment of the novel gel liner similar to the embodiment depicted in FIG. 1 but where the fabric is embedded in the gel.
Figure 5:
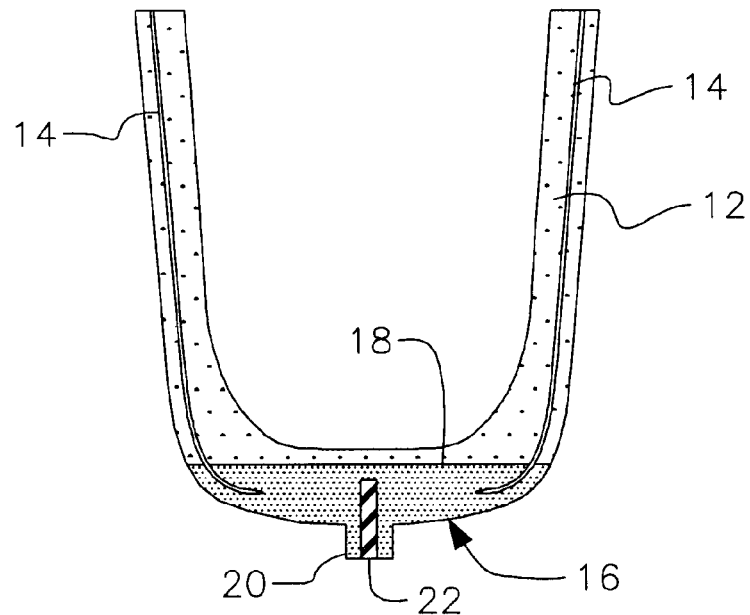
FIG. 5 is a sectional view of an embodiment of the novel gel liner similar to the embodiment depicted in FIG. 2 but where the fabric is embedded in the gel.
Figure 6:
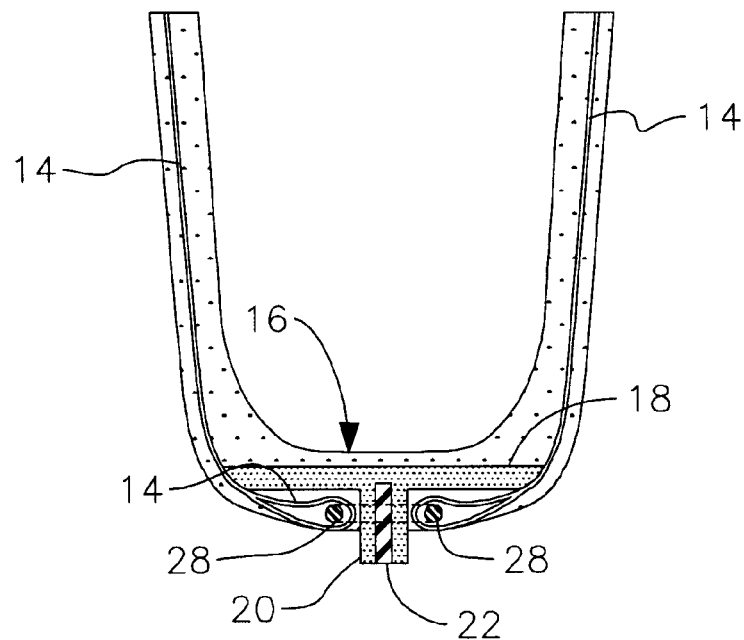
FIG. 6 is a sectional view of an embodiment of the novel gel liner similar to the embodiment depicted in FIG. 3 but where the fabric is embedded in the gel.

Yet another example of a suitable interconnection means is depicted in FIG. 3. The peripheral edge of fabric 14 that surrounds the central opening formed therein is positioned in underlying relation to a ring 28 which may be of metallic, textile or other suitable, substantially non flexible construction. The ring is then tightly pressed onto stem 20 to secure the fabric to the distal umbrella. As is understood from an inspection of FIG. 3, this attachment method has utility in the context of embedded and non-embedded bases.

Fabric 14 can be exterior to the gel or embedded in the gel. The fabric may also be extended to cover the entire length of the liner. In a preferred embodiment, the length of fabric 14 along the longitudinal axis is limited to three to six inches from the distal free end. This is sufficient to virtually eliminate pistoning, and by leaving the proximal end unreinforced the elongation of the liner is not limited by the fabric.

In another embodiment, the fabric is a double layer of fabric. The two layers of fabric are joined to one another by stitching or by an elastic adhesive and are secured to the exterior surface of the gel by either of the same means. The double layer of fabric may also be embedded within gel 12. These constructions provide an exceptional bond between fabric 14 and gel 12.

The preferred fabric is a nylon-lycra textile combination. A typical combination includes a nylon content in the range of 85% to 95% and a lycra content in the range of 5% to 15%. The preferred textile construction is the tricot type or the ribbed type having ribs running along the longitudinal axis.

To manufacture the novel liner, the fabric is held against the internal cavity of a mold and the gel is injected between a mandrel and the fabric. Accordingly, there is no need to turn the liner inside-out at the completion of the process. Gel is injected through central bore 22 of stem 20 to create the thick pad of gel at the distal end of the liner.

In view of these examples, it is clear that additional attachment means may be used, all of which are within the scope of this invention. The particular attachment means are not, per se, the most important aspects of the invention. In view of the examples provided, a good machine designer could develop numerous other attachment means not requiring grommets, annular grooves, or rings. The most important aspect of the invention is the mounting of the base of the distal umbrella either in embedded relation to the gel as in the first embodiment or to the exterior surface of said gel, in underlying relation to the fabric, as in the second embodiment. The mountings disclosed herein are superior to the mountings heretofore known where the distal umbrella is attached to the exterior surface of the fabric.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A prosthetic liner made of gel, comprising:
   a fabric secured to an exterior surface of said gel near a distal end of said liner, in overlying relation thereto, to limit pistoning of a distal end of a residual limb during ambulation;
   a distal umbrella secured at said distal end of said liner to enable connection of said liner to a prosthetic device;
   said distal umbrella having a base and a stem;
   said base being embedded in said gel; and
   an opening formed in said fabric through which extends said stem.

2. The prosthetic liner of claim 1, wherein said fabric is secured to an exterior surface of said gel in the region of said distal end, extending from said distal end a distance between about three to six inches from said distal end toward a proximal end of said prosthetic liner.

3. The prosthetic liner of claim 1, wherein said fabric is a single layer of fabric that is stitched to said exterior surface of said gel.

4. The prosthetic liner of claim 1, wherein said fabric is a single layer of fabric that is adhered to said exterior surface of said gel.

5. The prosthetic liner of claim 1, wherein said fabric is a double layer of fabric including a first layer of fabric and a second layer of fabric, and wherein said first and second layers of fabric are joined to one another and to said exterior surface of said gel.

6. The prosthetic liner of claim 5, wherein said first and second layers of fabric are stitched to one another and to said exterior surface of said gel.

7. The prosthetic liner of claim 5, wherein said first and second layers of fabric are adhered to one another and to said exterior surface of said gel.

8. The prosthetic liner of claim 1, further comprising a centrally apertured grommet means that is slideably received on said stem, said grommet means having jaws adapted to retain a peripheral edge of said fabric that surrounds said opening when said jaws are crimped together.

9. The prosthetic liner of claim 8, wherein said grommet means is a plastic grommet member that is bonded to said fabric by melting.

10. The prosthetic liner of claim 8, wherein said grommet means is a plastic grommet member that is bonded to said fabric by high frequency welding.

11. The prosthetic liner of claim 1, further comprising a ring tightly secured about said stem, a lowermost peripheral edge of said fabric being secured to said stem when disposed in underlying relation to said ring.

12. A prosthetic liner made of gel, comprising:
   a fabric embedded within said gel near a distal end of said liner to limit pistoning of a distal end of a residual limb during ambulation;
   a distal umbrella secured at said distal end of said liner to enable connection of said liner to a prosthetic device;
   said distal umbrella having a base and a stem;
   said base being embedded in said gel; and
   an opening formed in said fabric though which extends said stem.

13. The prosthetic liner of claim 12, wherein said fabric is embedded within said liner in the region of said distal end, extending from said distal end a distance between about three to six inches from said distal end toward a proximal end of said prosthetic liner.

14. The prosthetic liner of claim 12, wherein said fabric is a single layer of fabric.

15. The prosthetic liner of claim 12, wherein said fabric is a double layer of fabric including a first layer of fabric and a second layer of fabric that are joined to one another.

16. The prosthetic liner of claim 15, wherein said first and second layers of fabric are stitched to one another.

17. The prosthetic liner of claim 15, wherein said first and second layers of fabric are adhered to one another.

18. The prosthetic liner of claim 12, further comprising a centrally apertured grommet means that is slideably received on said stem, said grommet means having jaws adapted to retain a peripheral edge of said fabric that surrounds said opening when said jaws are crimped together.

19. The prosthetic liner of claim 18, wherein said grommet means is a plastic grommet member that is bonded to said fabric by melting.

20. The prosthetic liner of claim 18, wherein said grommet means is a plastic grommet member that is bonded to said fabric by high frequency welding.

21. The prosthetic liner of claim 12, further comprising a ring tightly secured about said stem a lowermost peripheral edge of said fabric being secured to said stem, when disposed in underlying relation to said ring.

* * * * *